United States Patent [19]

McMahon

[11] 3,948,992

[45] Apr. 6, 1976

[54] OXIDATION OF HYDROCARBONS IN THE PRESENCE OF SYNERGISTIC COMBINATION OF INITIATORS

[75] Inventor: Matthew A. McMahon, Wappingers Falls, N.Y.

[73] Assignee: Texaco Inc., New York, N.Y.

[22] Filed: Jan. 26, 1973

[21] Appl. No.: 327,039

[52] U.S. Cl. ......... 260/586 P; 260/592; 260/597 R; 260/617 H; 260/618 C; 260/631 R; 260/632 C; 260/632 N
[51] Int. Cl.² ............... C07C 27/12; C07C 29/00; C07C 45/02
[58] Field of Search ......... 260/586 B, 586 P, 597 R, 260/590, 592, 617 H, 618 C, 631 R, 632 C, 632 N

[56] References Cited
UNITED STATES PATENTS

| | | | |
|---|---|---|---|
| 2,557,282 | 6/1951 | Hamblet et al. | 260/586 B |
| 2,770,637 | 11/1956 | Mitchell | 260/586 B |
| 3,154,586 | 10/1964 | Bander et al. | 260/586 B |
| 3,458,582 | 7/1969 | Lachowicz et al. | 260/597 R |
| 3,655,769 | 4/1972 | McMahon | 260/597 R |

*Primary Examiner*—Norman Morgenstern
*Attorney, Agent, or Firm*—T. H. Whaley; C. G. Ries; Carl G. Seutter

[57] ABSTRACT

Hydrocarbons, such as cyclohexane, may be oxidized to products such as cyclohexanol, in the presence of oxidation initiator containing (i) a hydroperoxide R'OOH, such as t-butyl hydroperoxide, and (ii) a nitrogen oxide $NO_x$.

14 Claims, No Drawings

OXIDATION OF HYDROCARBONS IN THE PRESENCE OF SYNERGISTIC COMBINATION OF INITIATORS

FIELD OF THE INVENTION

This invention relates to the oxidation of hydrocarbons. More particularly, it relates to the oxidation of hydrocarbons in the presence of novel initiator systems.

BACKGROUND OF THE INVENTION

As is well known to those skilled in the art, hydrocarbons may be oxidized to yield a variety of products typified by alcohols, ketones, aldehydes, acids, etc. Among the problems which have been encountered in such processes are (i) the problem of control of the reaction to yield preferred products; (ii) the problem of initiating the reaction to permit attainment of satisfactory yields of product by reaction at moderate conditions; and (iii) the problem of increasing the rate of oxidation so as to minimize the size of the reactor required to produce desired amount of product.

OBJECTS OF THE INVENTION

It is an object of this invention to provide a process for preparing oxidation products of hydrocarbons. Other objects will be apparent to those skilled in the art.

STATEMENT OF THE INVENTION

In accordance with certain of its aspects, the process of this invention for preparing oxidation products of hydrocarbons may comprise oxidizing said hydrocarbons in the presence of an oxidation initiator containing an initiating quantity of (i) a hydroperoxide, typically R'OOH wherein R' is selected from the group consisting of alkyl, aralkyl, and cycloalkyl, and (ii) nitrogen oxides, $NO_x$, wherein $x$ is 1–2 thereby forming oxidation products of hydrocarbons; and recovering said oxidation products of hydrocarbons.

DESCRIPTION OF THE INVENTION

The hydrocarbons which may be oxidized by the process of this invention may be characterized by the formula RH. In the above compound, R may be hydrocarbon radical selected from the group consisting of alkyl, aralkyl, and cycloalkyl including such radicals when inertly substituted. When R is alkyl, it may typically be methyl, ethyl, n-propyl, iso-propyl, n-butyl, i-butyl, sec-butyl, amyl, octyl, decyl, octadecyl, etc. When R is aralkyl, it may typically be benzyl, beta-phenylethyl, etc. When R is cycloalkyl, it may typically be cyclohexyl, cycloheptyl, cyclooctyl, 2-methylcycloheptyl, 3-butycyclohexyl, 3-methylcyclohexyl, etc. R may be inertly substituted i.e. it may bear a non-reactive substituent such as aryl, halogen, nitro, carboxyl, etc. Typically inertly substituted R groups may include 3-chloropropyl, p-chlorobenzyl, etc. The preferred R groups may be lower alkyl, i.e. $C_1-C_{10}$ alkyl, groups including eg methyl, ethyl, n-propyl, i-propyl, butyls, amyls, hexyls, octyls, decyls, etc. R may be preferably cyclohexyl.

Typical hydrocarbons which may be oxidized by the process of this invention may be butane, pentane, hexane, octanes, etc. The process of this invention is particularly characterized by its ability to oxidize naphthenes, including cyclohexane, methyl cyclohexane, cyclopentane, methyl cyclopentane, etc. and aromatics such as toluene, xylene, n-propyl benzene etc. The preferred hydrocarbon charge may be a cyclohexane and preferably cyclohexane per se.

It is a feature of the process of this invention that oxidation of the charge hydrocarbon RH is carried out in the presence of an oxidation initiator containing an initiating quantity of a hydroperoxide and a nitrogen oxide.

The hydroperoxide, which may be used as a component of the oxidation initiator in practice of the process of this invention, may be characterized by the formula R'OOH wherein R' may be selected from the same group as that from which R is selected. R' may typically be different from R; in the preferred embodiment R' may be a tertiary hydrocarbon moiety so that the hydroperoxide is a tertiary hydroperoxide in which one oxygen is bonded to a carbon atom which bears no hydrogen eg. t-butyl; 1,1-dimethylpropyl; etc.

Illustrative hydroperoxides may include the following:

n-butyl hydroperoxide
t-butyl hydroperoxide
cyclohexyl hydroperoxide
iso-butyl hydroperoxide
benzyl hydroperoxide
cumene hydroperoxide The preferred hydroperoxide may be a tertiary hydroperoxide, most preferably t-butyl hydroperoxide.

The nitrogen oxide which may be used as a component of the oxidation inhibition in practice of the process of this invention may be characterized by the formula $NO_x$, wherein $x$ is 1–2.

The preferred method of forming the desired nitrogen oxide may be by the reaction $2NO+O_2 \rightarrow 2NO_2$; and it will be apparent to those skilled in the art that $NO_2$ will be in equilibrium with $N_2O_4$ viz. $2NO_2 \rightleftharpoons N_2O_4$. In the preferred embodiment, the nitrogen oxides may be prepared in this manner; and the mixture used may thus contain equilibrium proportions of NO, $NO_2$, and $N_2O_4$. Considering $N_2O_4$ as its equivalent $NO_2$, the net mixture will conform to the formula $NO_x$ wherein $x$ is 1–2.

The initiating quantity (in moles) of oxidation initiator, per 100 moles of charge hydrocarbon, may be as follows:

| Oxidation Initiator | Broad Range | Preferred Range | Typical |
|---|---|---|---|
| R'OOH | 0.1–10 | 0.5–2.0 | 1.5 |
| $NO_x$ | 0.01–10 | 0.1–1.0 | 0.25 |
| Total | 0.11–20 | 0.6–3.0 | 1.75 |

In practice of the process of this invention, there may be admitted to the reaction zone, an oxygen-containing gas in amount to provide 1–25 moles, preferably 5–10 moles, say 10 moles of oxygen per 100 moles of charge hydrocarbon, eg cyclohexane. Typically this may be admitted as air, oxygen-enriched air, or more preferably oxygen of 90–100% purity.

Preferably the oxidation of the hydrocarbon may be carried out at 75°–200°C, typically 100°–150°C, say 125°C. and 0–300 psig, typically 0–75 psig, say 30 psig for 15–180 minutes, typically 30–100 minutes, say 60 minutes.

During reaction, it is a feature of the process of this invention that the hydrocarbon may be oxidized to a product mixture containing little or no organic nitrate or nitro-organic compounds (usually less than about 10% by weight and very commonly substantially no measurable organic nitrogen compounds). It may normally be found that the oxidized hydrocarbon is exclusively converted to compounds typified by alcohols and ketones.

In typical oxidation of cyclohexane for example, it may be found that the oxidized charge composition is converted, in yield of substantially 100%, to cyclohexanol and cyclohexanone. Presence of only the hydroperoxide alone yields small amounts of desired products, and presence of only the $NO_x$ alone yields only small amounts of desired products — at typical reaction temperature of 125°C during 1 hour.

Product mixture may be recovered as by degassing the condensed product to remove gaseous by-products including unreacted nitrogen oxides, and separating the oxygenated product by distillation or by taking advantage of different solubilities in eg water (as in the case of cyclohexanone and cyclohexane).

Practice of the process of this invention may permit attainment of product in yield of 1–20%, say 10% of the charge.

DESCRIPTION OF PREFERRED EMBODIMENT

Practice of the process of this invention may be apparent to those skilled in the art from the following wherein as elsewhere in this description, all parts are parts by weight unless otherwise stated.

EXAMPLES I–VII pressure drop was observed. The ampoule was then sealed and allowed to warm to room temperature. The ampoules were then heated in an oven equipped with a rocking device (173 rpm) which caused the ampoule to rock ± 45° in each revolution. It usually took about 8 minutes for the sample to reach the temperature of the oven. It was possible to maintain the oven at ± 1°C of the desired temperature. After the desired reaction period, the ampoules were removed from the oven, cooled in liquid nitrogen and opened. The contents of the ampoules were then poured into a vial containing a small amount of anhydrous sodium sulfate. The samples were then analyzed by gas chromatography.

Mixtures of nitrogen oxides in oxygen were prepared by filling a 2-liter bulb to a known pressure with nitric oxide. The bulb was then filled with oxygen to a pressure of 760 mm. After 15 minutes of reaction time was allowed, the bulb was pressured to 760 mm. again with oxygen. After waiting another 15 minutes, the entire rack was filled with the gas mixture to a pressure of 380 mm. The desired amount of the gas mixture was introduced into the ampoule in the same manner that the oxygen was introduced.

All gas chromatographic analysis of liquid reaction mixtures were done with a Varian-Aerograph Instrument (model 204B) equipped with hydrogen flame detectors. A 6 ft × ⅛ inch stainless steel column packed with 15 percent Igepal, Co 990 on Aw Chromasorb W was used to analyze the cyclohexane oxidation mixtures. The conditions used for this separation were:

Column Temperature — 115°–130°C.
Injector Temperature — 150°C.
Detector Temperature — 200°C.
Helium Flow Rate — 70 percent

TABLE

The Effect of $NO_x$ on the Initiating Effectiveness of t-Butyl Hydroperoxide

| | CHARGE | | | PRODUCTS | | | | |
|---|---|---|---|---|---|---|---|---|
| Run No.[1] | $O_2$ mmoles | $NO_x$ mmoles | TOOH moles/l | =O | -OH | $ONO_2$ | $NO_2$ | Total Oxidation Products Wt % |
| I* | 1.5 | 0.006 | 0.0 | 0.0 | 0.0 | 0.0 | 0.0 | 0.0 |
| II* | 1.0 | 0.0 | 0.146 | 0.29 | 0.42 | 0.0 | 0.0 | 0.71 |
| III | 0.99 | 0.01 | 0.146 | 0.71 | 0.80 | 0.0 | 0.0 | 1.51 |
| IV | 0.94 | 0.06 | 0.146 | 0.73 | 1.48 | 0.0 | 0.0 | 2.21 |
| V | 0.88 | 0.12 | 0.146 | 0.69 | 1.56 | 0.0 | 0.0 | 2.25 |
| VI* | 0.90 | 0.10 | 0.0 | 0.37 | 0.52 | 0.09 | Tr | 0.89 |
| VII* | 0.94 | 0.06 | 0.0 | 0.27 | 0.50 | 0.11 | Tr | 0.89 |

[1]About 2g of cyclohexane was charged to each ampoule.
All ampoules were heated for one hour at 125°C.
T = tertiary butyl
*Control Run - others are experimental.

In this series of comparative examples, all oxidation runs were made in ampoules with an internal volume of 15–16 ml. In a usual run, about 2 grams of the solution to be charged was charged to an ampoule by means of a syringe equipped with a long needle tip. The ampoule was then attached to the vacuum rack, the contents of the tube frozen in liquid nitrogen and evacuated to a pressure of 0.005 mm/Hg or less. Oxygen was then charged to the ampoules by first filling the entire vacuum rack (whose volume is known) with oxygen to a pressure of 380 mm and sharing this oxygen with the previously-cooled evacuated ampoule until the desired From the above table, it will be apparent that in the absence of t-butyl hydroperoxide (Control Example I), no reaction occurred; in the absence of $NO_x$ (control Example II), only small amounts of the desired products may be obtained. As the concentration of $NO_x$ alone increased (control Examples I, VI, and VII), the concentration of undesirable nitrogencontaining products increased to 0.09/(0.09 + 0.52 + 0.37) = 9% and 0.11/(0.11 + 0.50 + 0.27) = 12.5%.

When both t-butyl hydroperoxide and $NO_x$ initiator are present (Examples III, IV, V), the amount of nitrogencontaining product is zero; the amount of total oxidation products increases by a factor of 2–3; and the ratio of alcohol to ketone formed desirably increases to as much as 2+.

Results comparable to those of experimental Examples III-V may be achieved by use of the following hydroperoxides in combination in the initiator;

VIII cumene hydroperoxide
IX 1,1-dimethyl propane hydroperoxide
X benzoyl hydroperoxide
XI benzyl hydroperoxide Although this invention has been illustrated by reference to specific embodiments, it will be apparent to those skilled in the art that various changes and modifications may be made which clearly fall within the scope of this invention.

I claim:

1. The process for preparing an oxidation product of an alkyl, aralkyl, or cycloalkyl hydrocarbon which comprises oxidizing said hydrocarbon at 75°–200°C in the presence of (i) an oxygen containing gas and (ii) an oxidation initiator containing an initiating quantity of an alkyl, aralkyl, or cycloalkyl hydroperoxide and a nitrogen oxide thereby forming said oxidation product of said hydrocarbon; and recovering said oxidation product of said hydrocarbon.

2. The process for preparing an oxidation product of a hydrocarbon as claimed in claim 1 wherein said hydrocarbon is a naphthene.

3. The process for preparing an oxidation product of a hydrocarbon as claimed in claim 1 wherein said hydrocarbon is cyclohexane.

4. The process for preparing an oxidation product of a hydrocarbon as claimed in claim 1 wherein said hydroperoxide is an alkyl hydroperoxide.

5. The process for preparing an oxidation product of a hydrocarbon as claimed in claim 1 wherein said hydroperoxide is a tertiary hydroperoxide.

6. The process for preparing an oxidation product of a hydrocarbon as claimed in claim 1 wherein said hydroperoxide is tertiary-butyl hydroperoxide.

7. The process for preparing an oxidation product of a hydrocarbon as claimed in claim 1 wherein said nitrogen oxide includes $NO_x$ wherein $x$ is 1–2.

8. The process for preparing an oxidation product of a hydrocarbon as claimed in claim 1 wherein said nitrogen oxide contains at least one member is selected from the group consisting of nitric oxide NO, nitrogen dioxide $NO_2$, and nitrogen tetroxide $N_2O_4$.

9. The process for preparing an oxidation product of a hydrocarbon as claimed in claim 1 wherein said oxidation initiator is present in initiating quantity of 0.6–3.0 moles per 100 moles of charge hydrocarbon.

10. The process for preparing an oxidation product of a hydrocarbon as claimed in claim 1 wherein said nitrogen oxide consists essentially of nitric oxide and its equilibrium oxidation products.

11. The process for preparing an oxidation product of a hydrocarbon as claimed in claim 1 wherein said hydroperoxide is present in amount of 0.5–2.0 moles per 100 moles of charge hydrocarbon.

12. The process for preparing an oxidation product of a hydrocarbon as claimed in claim 1 wherein said nitrogen oxide is present in amount of 0.1–1.0 moles per 100 moles of charge hydrocarbon.

13. The process for oxidizing an alkyl, cycloalkyl or aralkyl hydrocarbon to form therefrom an oxidation product containing alcohols and carbonyl compounds which comprises oxidizing said hydrocarbon at 75°–200°C and 0–75 psig in the presence of (1) an oxygen containing gas and (ii) an oxidation initiator containing, per 100 moles of hydrocarbon charge, 0.1–10 moles of tertiary butyl hydroperoxide and 0.01–10 moles of nitrogen oxides thereby forming said oxidation product of said hydrocarbon; and recovering said oxidation product of said hydrocarbon.

14. The process as claimed in claim 13 for oxidizing cyclohexane to form an oxidation product containing cyclohexanol and cyclohexanone which comprises oxidizing said cyclohexane at 75°–200°C in the presence of (i) an oxygen containing gas and (ii) an oxidation initiator containing, per 100 moles of hydrocarbon charge 0.1–10 moles of nitrogen oxides, formed by the reaction of nitric oxide and oxygen, thereby forming said oxidation product; and recovering said oxidation product.

* * * * *